(12) United States Patent
Navab et al.

(10) Patent No.: US 7,198,404 B2
(45) Date of Patent: Apr. 3, 2007

(54) REAL-TIME ACQUISITION OF CO-REGISTERED X-RAY AND OPTICAL IMAGES

(75) Inventors: Nassir Navab, Munich (DE); James P. Williams, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 150 days.

(21) Appl. No.: 10/812,631

(22) Filed: Mar. 30, 2004

(65) Prior Publication Data

US 2004/0247076 A1 Dec. 9, 2004

Related U.S. Application Data

(60) Provisional application No. 60/460,086, filed on Apr. 3, 2003.

(51) Int. Cl.
*A61B 6/08* (2006.01)
(52) U.S. Cl. .......................................... 378/206; 378/63
(58) Field of Classification Search .................. 378/63, 378/206
See application file for complete search history.

(56) References Cited

U.S. PATENT DOCUMENTS

| | | | | | |
|---|---|---|---|---|---|
| 2,474,421 | A | * | 6/1949 | Hollstein ..................... | 378/152 |
| 4,246,607 | A | * | 1/1981 | Vijverberg ................. | 378/98.5 |
| 5,320,111 | A | * | 6/1994 | Livingston .................. | 600/567 |
| 5,419,320 | A | | 5/1995 | Kawaguchi et al. ........ | 128/633 |
| 5,539,798 | A | * | 7/1996 | Asahina et al. ............ | 378/98.5 |
| 5,590,170 | A | * | 12/1996 | Zweig ........................ | 378/63 |
| 5,606,590 | A | * | 2/1997 | Petersen et al. ............ | 378/177 |
| 5,644,616 | A | * | 7/1997 | Landi et al. ................. | 378/206 |
| 5,892,808 | A | * | 4/1999 | Goulding et al. ............. | 378/63 |
| 6,227,704 | B1 | * | 5/2001 | Bani-Hashemi et al. ..... | 378/206 |
| 6,229,873 | B1 | * | 5/2001 | Bani-Hashemi et al. ...... | 378/63 |

(Continued)

OTHER PUBLICATIONS

SU 883 725 A (INST BIOLQGICHESKOI FIZ) Nov. 23, 1981 figure 1 & Database WPI Section EI, Week 198237 Derwent Publications Ltd., London, GB; Class S03, AN 1982—M2851E abstract.

(Continued)

*Primary Examiner*—Edward J. Glick
*Assistant Examiner*—Thomas R. Artman
(74) *Attorney, Agent, or Firm*—Donald B. Paschburg; F. Chau & Associates, LLC

(57) ABSTRACT

An apparatus, method and program storage device are provided for co-registration of multi-modal images in a three-dimensional environment, where the apparatus includes a source of excitation light, an electromagnetic-ray source disposed relative to the source of excitation light, an electromagnetic-ray transparent mirror having a first surface disposed towards the excitation light and a second surface disposed towards the electromagnetic-ray source, a target location disposed towards the first surface of the electromagnetic-ray transparent mirror for locating a target and receiving the excitation light and the electromagnetic rays, an electromagnetic-ray detector disposed on an opposite side of the target location relative to the electromagnetic-ray transparent mirror for detecting electromagnetic-rays transmitted through the target, a second electromagnetic-ray transparent mirror having a light-reflective surface disposed towards the target location, and a light detector disposed towards the light-reflective surface of the second electromagnetic-ray transparent mirror for detecting light from the target.

21 Claims, 3 Drawing Sheets

U.S. PATENT DOCUMENTS

| | | | |
|---|---|---|---|
| 6,267,502 B1 * | 7/2001 | McNeirney et al. | 378/206 |
| 6,404,846 B1 * | 6/2002 | Hasegawa et al. | 378/44 |
| 6,447,163 B1 * | 9/2002 | Bani-Hashemi et al. | 378/205 |
| 6,473,489 B2 * | 10/2002 | Bani-Hashemi et al. | 378/63 |
| 6,478,462 B2 * | 11/2002 | Polkus et al. | 378/207 |
| 6,614,875 B2 * | 9/2003 | Suuronen | 378/63 |
| 6,731,718 B2 * | 5/2004 | Ogura et al. | 378/63 |
| 6,869,218 B2 * | 3/2005 | Winsor | 378/207 |

OTHER PUBLICATIONS

Kohen Elli et al: Combined fluorescence and ultrastructural mapping of living cell Proc SPIE Int Soc Opt Eng; Proceedings of SPIE—The International Society for Optical Engineering 1990 Publ by Int Soc for Optical Engineering, Bellingham, WA, USA, vol. 1204 PT 2, 1990, pp. 736-752, XP008034681 p. 750; figure 15.

* cited by examiner

REAL-TIME ACQUISITION OF CO-REGISTERED X-RAY AND OPTICAL IMAGES

CROSS-REFERENCE TO RELATED APPLICATION

This application claims the benefit of U.S. Provisional Application Ser. No. 60/460,086, filed Apr. 3, 2003 and entitled "System and Method for Real-Time Acquisition of Co-Registered X-Ray and Optical (Fluorescence, Coherent, Diffused or Transmission) Images", which is incorporated herein by reference in its entirety.

BACKGROUND

The present disclosure is directed towards systems and methods for acquiring co-registered X-ray and optical imagery. Medical image data, for example, is typically desired and/or obtained through various types of imaging modalities.

A co-pending U.S. patent application Ser. No. 10/001,552, entitled "System and Method for Highlighting a Scene Under Vision Guidance", which is subject to the same duty of assignment as the present application, discloses a system and method for processing coordinates of a target point in a captured image of a real scene, and converting the image coordinates into the coordinates of a light projector to illuminate the target point. In addition, issued U.S. Pat. Nos. 6,227,704; 6,229,873; 6,447,163 and 6,473,489; which are also subject to the same duty of assignment as the present application, disclose systems and methods for acquisition of video and X-ray images.

What is needed is a new system and method for real-time acquisition of co-registered optical (e.g., fluorescence, coherent, diffused or transmission) and X-ray images. Such a system could provide physicians with new imaging abilities for applications including, for example, Arthritis treatment monitoring. For such an application, an optical image could show the enzyme activities, while a co-registered X-ray image could allow a physician to exactly locate the activity in relation to bone structure. In this way, a physician could take advantage of both imaging systems at the same time, by viewing the superimposed images, and thereby be relieved from having to relate the two types of images in his/her mind. The desired system could allow the physician to visualize each of the optical or X-ray images alone or in combination with a co-registered image. The present disclosure addresses these and other related issues.

SUMMARY

These and other drawbacks and disadvantages of the prior art are addressed by an apparatus, method and program storage device for co-registration of multi-modal images in a three-dimensional environment.

A first embodiment apparatus for co-registration of multi-modal images in a three-dimensional environment includes a source of excitation light, a one-way mirror having a transmissive side disposed towards the excitation light for transmitting the excitation light and a reflective side for reflecting light received from a target, an electromagnetic-ray source disposed relative to the source of excitation light, an electromagnetic-ray transparent mirror having a light-reflective surface disposed towards a reflecting side of the one-way mirror and an electromagnetic-ray transmissive surface disposed towards the electromagnetic-ray source, a target location disposed towards the light-reflective surface of the electromagnetic-ray transparent mirror for locating a target and receiving the excitation light and the electromagnetic-rays, an electromagnetic-ray detector disposed on an opposite side of the target location relative to the electromagnetic-ray source for detecting electromagnetic-rays transmitted through the target, and a light detector disposed towards the reflective side of the one-way mirror for detecting light from the target.

A second embodiment apparatus for co-registration of multi-modal images in a three-dimensional environment includes a source of excitation light, an electromagnetic-ray source disposed relative to the source of excitation light, an electromagnetic-ray transparent mirror having a first surface disposed towards the excitation light and a second surface disposed towards the electromagnetic-ray source, a target location disposed towards the first surface of the electromagnetic-ray transparent mirror for locating a target and receiving the excitation light and the electromagnetic rays, an electromagnetic-ray detector disposed on an opposite side of the target location relative to the electromagnetic-ray transparent mirror for detecting electromagnetic-rays transmitted through the target, a second electromagnetic-ray transparent mirror having a light-reflective surface disposed towards the target location, and a light detector disposed towards the light-reflective surface of the second electromagnetic-ray transparent mirror for detecting light from the target.

These and other aspects, features and advantages of the present disclosure will become apparent from the following description of exemplary embodiments, which is to be read in connection with the accompanying drawings.

BRIEF DESCRIPTION OF THE DRAWINGS

The present disclosure teaches an apparatus and method for image segmentation in a three-dimensional environment, in accordance with the following exemplary figures, in which.

DETAILED DESCRIPTION OF PREFERRED EMBODIMENTS

The present disclosure introduces a system and method for real-time acquisition of co-registered X-ray and optical images, including, for example, fluorescence, coherent, diffused or transmission images. System embodiments provide physicians with new imaging capabilities applicable to many applications, including, for example, Arthritis treatment monitoring.

In an Arthritis treatment monitoring example, the optical image shows the enzyme activities. The co-registered X-ray image allows the physician to precisely locate the enzyme activities in relation to the bone structure of the patient. In this way, the different types of images are superimposed so that the physician may take advantage of both imaging systems at the same time without the need to relate the two images manually. A preferred system embodiment permits the physician to visualize each of the optical or X-ray images alone, or combined into one co-registered image.

In the description that follows, an X-ray or X-ray fluoroscopy system is illustrated with its two main components: a) X-ray source; and b) X-ray detector. An optical imaging device is also illustrated by its two main components: a) source of excitation light; and b) detector of emitted, reflected, diffused or transmitted light.

Figure 1:
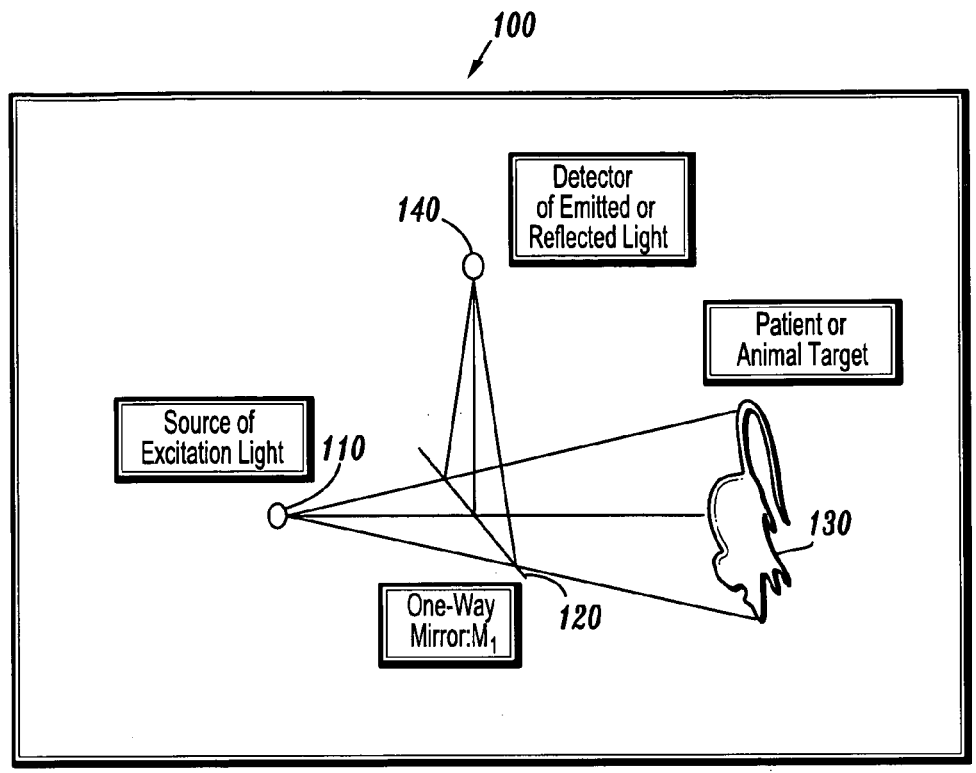
FIG. 1 shows a schematic diagram of an optical imaging system where the source of the excitation light and the optical camera detecting the emitted or reflected light have the same projection geometry.

As shown in FIG. 1, a first exemplary optical imaging system is indicated generally by the reference numeral 100. The imaging system 100 includes a source of excitation light 110 projecting through a non-reflecting side of a one-way mirror 120 to a target 130. The light emitted or reflected from the target 130 is reflected by a reflecting side of the one-way mirror to a detector of emitted or reflected light 140. Thus, in the optical imaging system 100, the source of the excitation light and the optical camera detecting the emitted or reflected light have the same projection geometry.

Figure 2:
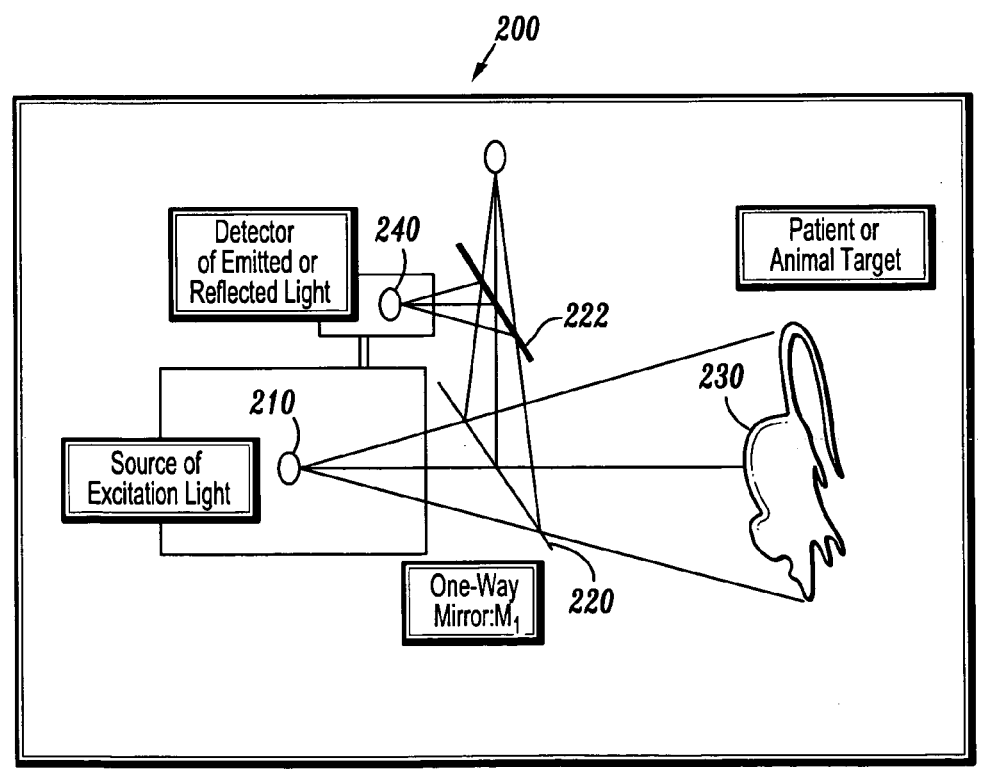
FIG. 2 shows a schematic diagram of an optical imaging system where the source of the excitation light and the optical camera detecting the emitted or reflected light have the same projection geometry, and are each on the same side and attached side-by-side.

Turning to FIG. 2, a second exemplary optical imaging system is indicated generally by the reference numeral 200. The imaging system 200 includes a source of excitation light 210 projecting through a non-reflecting side of a one-way mirror 220 to a target 230. The light emitted or reflected from the target 230 is reflected by a reflecting side of the one-way mirror to a mirror 222, which reflects the light to a detector of emitted or reflected light 240. Thus, in the optical imaging system 200, the source of the excitation light and the optical camera detecting the emitted or reflected light have the same projection geometry. In addition, the source and the detector are on the same side and can be attached side-by-side.

Figure 3:
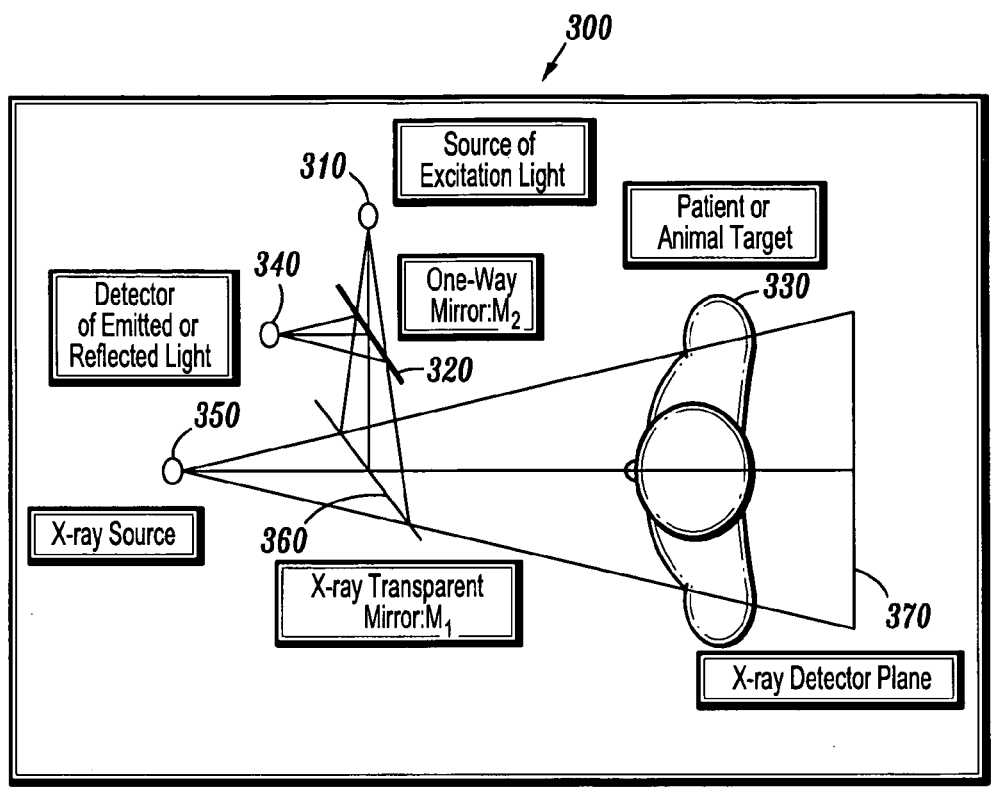
FIG. 3 shows a schematic diagram of a co-registered imaging system in accordance with an illustrative embodiment of the present disclosure where the excitation is done with a source of coherent light.

Turning now to FIG. 3, a first exemplary co-registered imaging system is indicated generally by the reference numeral 300. The imaging system 300 includes a source of excitation light 310 projecting through a non-reflecting side of a one-way mirror 320 to a mirror 360. The mirror 360 is an X-ray transparent mirror that reflects the light to a target 330. The light emitted or reflected from the target 330 is reflected by the mirror 360 to a reflecting side of the one-way mirror 320, which reflects the light to a detector of emitted or reflected light 340. The imaging system 300 further includes an X-ray source 350 projecting through the X-ray transparent mirror 360 to the target 330. An X-ray detector plate 370 receives the X-rays transmitted through the target 330.

Thus, the resulting system 300 provides co-registered X-ray and emitted or reflected images. In a case where the excitation is done with a source of coherent light, the detector detects the reflected light. In a case of fluorescence imaging, the detector will detect the emitted light from the object. Note that different detectors and special filters may be used for each of the imaging systems described herein.

Figure 4:
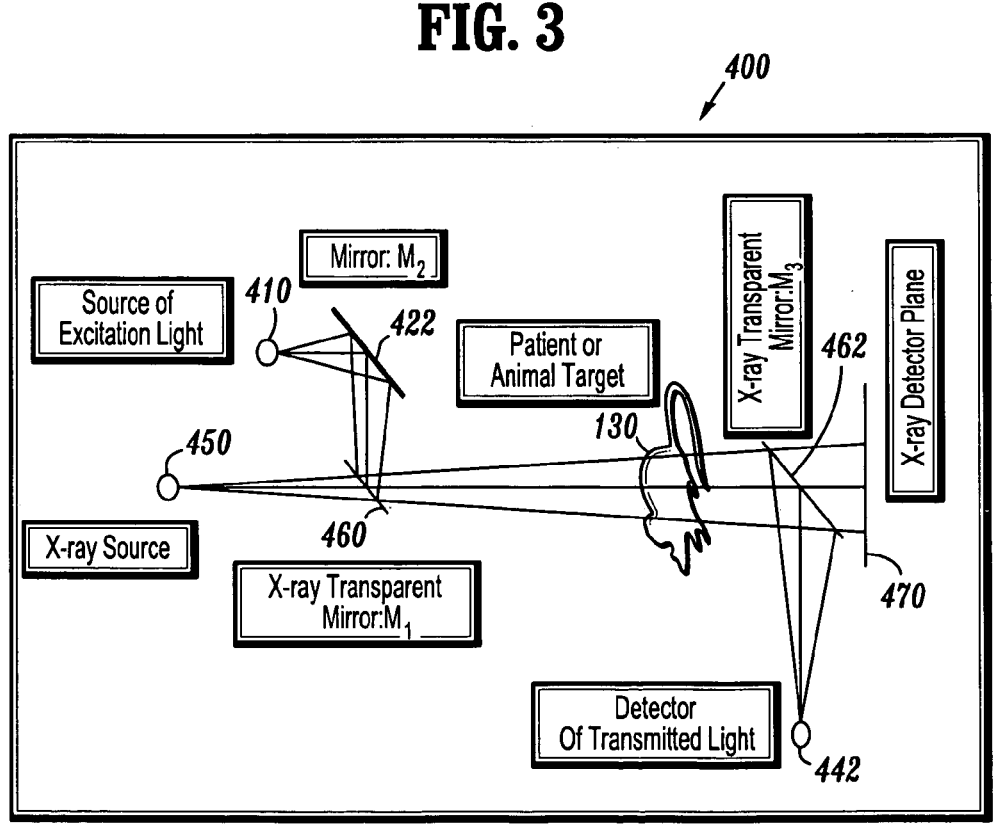
FIG. 4 shows a schematic diagram of a co-registered imaging system in accordance with an illustrative embodiment of the present disclosure where the detector of the transmitted light is positioned such that its images are co-registered with X-ray images.

As shown in FIG. 4, a second exemplary co-registered imaging system is indicated generally by the reference numeral 400. The imaging system 400 includes a source of excitation light 410 reflecting from a mirror 422. The light reflected from the mirror 422 to a mirror 460. The mirror 460 is an X-ray transparent mirror that reflects the light to a target 430. The light transmitted through the target 430 is reflected by another X-ray transparent mirror 462, which reflects the light to a detector of transmitted light 442. The imaging system 400 further includes an X-ray source 450 projecting through the X-ray transparent mirror 460 to the target 430. The light transmitted through the target 430 is further transmitted through the other X-ray transparent mirror 462. An X-ray detector plate 470 receives the X-rays transmitted through the target 430 and the other X-ray transparent mirror 462. Thus, in the system 400, the detector of the transmitted light is positioned in a way that the images it provides are co-registered with X-ray images.

Figure 5:
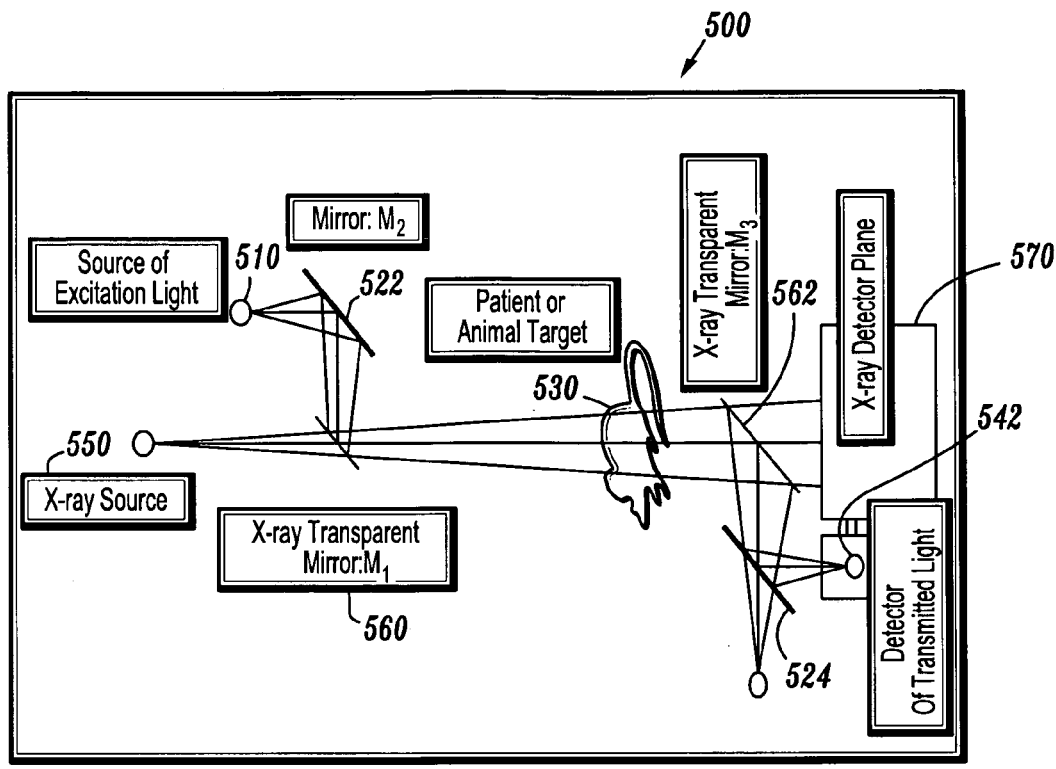
FIG. 5 shows a schematic diagram of a co-registered imaging system in accordance with an illustrative embodiment of the present disclosure where the detector of the transmitted light is positioned such that its images are co-registered with X-ray images and the detector is attached to the side of the X-ray detector.

Turning to FIG. 5, a third exemplary co-registered imaging system is indicated generally by the reference numeral 500. The imaging system 500 includes a source of excitation light 510 reflecting from a mirror 522. The light reflected from the mirror 522 to a mirror 560. The mirror 560 is an X-ray transparent mirror that reflects the light to a target 530. The light transmitted through the target 530 is reflected by another X-ray transparent mirror 562, which reflects the light to a detector of transmitted light 542. The imaging system 500 further includes an X-ray source 550 projecting through the X-ray transparent mirror 560 to the target 530. The light transmitted through the target 530 is further transmitted through the other X-ray transparent mirror 562 to another mirror 524. An X-ray detector plate 570 receives the X-rays transmitted through the target 530, the other X-ray transparent mirror 562 and the other mirror 524. Thus, in the system 500, the detector of the transmitted light is positioned in a way that the images it provides are co-registered with X-ray images, and this detector can be conveniently attached to the side of the X-ray detector.

Figure 6:
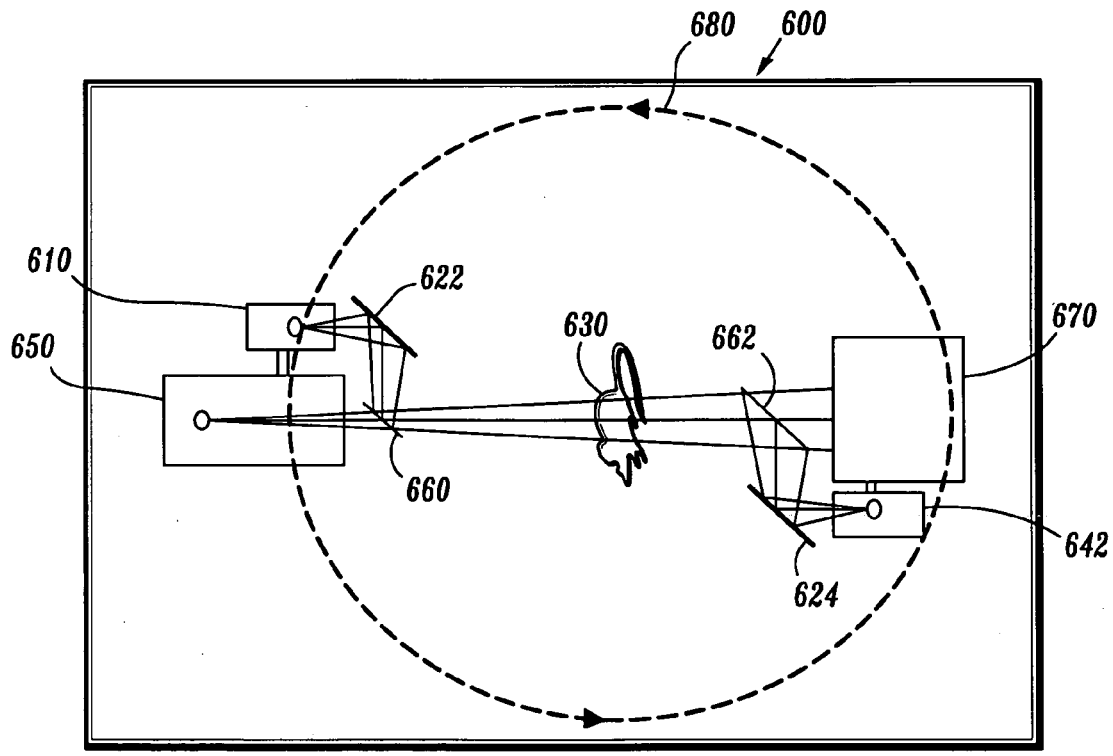
FIG. 6 shows a schematic diagram of a co-registered imaging system in accordance with an illustrative embodiment of the present disclosure where the system is capable of rotating by at least 200 degrees around a patient.

Turning now to FIG. 6, a fourth exemplary co-registered imaging system is indicated generally by the reference numeral 600. The imaging system 600 includes a source of excitation light 610 reflecting from a mirror 622. The light reflected from the mirror 622 to a mirror 660. The mirror 660 is an X-ray transparent mirror that reflects the light to a target 630. The light transmitted through the target 630 is reflected by another X-ray transparent mirror 662, which reflects the light to a detector of transmitted light 642. The imaging system 600 further includes an X-ray source 650 projecting through the X-ray transparent mirror 660 to the target 630. The light transmitted through the target 630 is further transmitted through the other X-ray transparent mirror 662 to another mirror 624. An X-ray detector plate 670 receives the X-rays transmitted through the target 630, the other X-ray transparent mirror 662 and the other mirror 624. The entire system 600, excluding the target 530, is mounted to gimbals, tracks or like devices for rotating about the centrally disposed target 530.

Thus, in a particularly preferred embodiment, the co-registered X-ray and Transmitted Optical Imaging system 600 rotates around the target or patient by at least 200 degrees, while acquiring X-ray and transmitted optical images. These images are then used for tomographic reconstruction. The two sets of resulting reconstructed 3D data are thus fully co-registered by design. This allows the physician to visualize the data as two separate data sets or one composite data set.

According to one aspect of the present disclosure, the image capture device and the illumination device comprise common optical properties. This may be realized by means of one one-way mirror. FIG. 1 provides an exemplary construction of such a system. FIG. 2 provides a second exemplary construction where the source and the detector can be attached side-by-side using an additional mirror.

In another aspect of this present disclosure, the system allows the acquisition of real-time X-ray and fluorescence or coherent optical imaging. FIG. 3, illustrates an exemplary construction of such a system. The system allows the user to choose a target to be illuminated in a real scene using X-ray image data of the same scene.

In one aspect, a method for illuminating a target point in a real scene comprises the steps of capturing X-ray image data of a scene, identifying X-ray image data associated with a target point, and projecting a light beam at the target point in the rear scene. The step of projecting comprises the steps of converting image coordinates of the target point to light coordinates for directing the light beam, and processing the light coordinates to direct the light beam to the target point in the real scene.

The illumination system and its control for embodiments of the present disclosure may be realized as described in the co-pending U.S. patent application Ser. No. 10/001,552, entitled "System and Method for Highlighting a Scene Under Vision Guidance". A difference here is that the system can also be guided by X-ray vision in cases where the target for illumination can be better defined in respect to the anatomical targets visible under X-rays. Once the target is illuminated, the reflected or the emitted light, in the case of fluorescence imaging, is captured by an optical sensor with the same imaging geometry as the X-ray imaging system. This allows the user, such as a physician, to see a composite image, which includes both information from X-ray and optical imaging. Such system embodiments can provide new imaging possibilities, which can play an important role in improving the diagnosis and treatment monitoring procedures for many diseases.

FIGS. 4 and 5 illustrate two other aspects of the present disclosure. In these cases the system co-registers the X-ray and transmitted optical imaging. The Transmitted Optical Imaging here is defined as a system composed of a light source, which emits the light rays towards an object of interest and a detector on the other side of the target, which measures the intensity of the transmitted light. This intensity is a function of the absorption of the tissues and/or material forming the object (for example see "Imaging through Random Media Using Low Coherence Optical Heterodyning" by A. Schmidt, R. Cotey, and P. Saulnier, Optics Letters, Volume 20, Number 4, Feb. 15, 1995). System embodiments of the present disclosure can use two, three or four mirrors, for example, depending on the choice of having the light source and transmitted light optical detector on the side, or orthogonal to, the X-ray source and detector, respectively.

According to another aspect of this present disclosure, the co-registered X-ray and Transmitted Optical Imaging system rotates around the patient or animal target by at least 200 degrees, while acquiring both X-ray and optical images. These images can then be used for tomographic reconstruction. The two sets of resulting reconstructed 3D data are thus fully co-registered. This allows the physician to visualize the data as two separate or one composite data set. The calibration and reconstruction from rotating C-arms have been extensively discussed in the literature. For example, the following U.S. patents propose different methods for calibration and tomographic reconstruction using such system: U.S. Pat. No. 6,049,582; U.S. Pat. No. 6,038,282; U.S. Pat. No. 5,963,613; U.S. Pat. No. 5,963,612; U.S. Pat. No. 5,923,727; U.S. Pat. No. 5,835,563 and U.S. Pat. No. 5,822,396. In preferred embodiments of the present disclosure, a particularly advantageous feature is in the co-registration of the X-ray and Transmitted Optical Imaging systems by the particular construction and calibration of this system. This allows obtaining co-registered 3D reconstruction data from these two modalities.

The relative placement of the elements of embodiments of the present disclosure are important. The X-ray imaging system, the optical imaging system, and the mirrors need to be placed correctly, as will be understood by those of ordinary skill in the pertinent art. There is also a feature for computing a transformation, taking into account the differences in the intrinsic imaging parameters of the X-ray and Optical images. These geometrical and imaging calibrations can be considered as modifications and improvements of those described in U.S. Pat. Nos. 6,473,489; 6,447,163; 6,229,873 and 6,227,704, for example.

These and other features and advantages of the present disclosure may be readily ascertained by one of ordinary skill in the pertinent art based on the teachings herein. It is to be understood that the teachings of the present disclosure may be implemented in various forms of hardware, software, firmware, special purpose processors, or combinations thereof.

Most preferably, the teachings of the present disclosure are implemented as a combination of hardware and software. Moreover, the software is preferably implemented as an application program tangibly embodied on a program storage unit. The application program may be uploaded to, and executed by, a machine comprising any suitable architecture. Preferably, the machine is implemented on a computer platform having hardware such as one or more central processing units ("CPU"), a random access memory ("RAM"), and input/output ("I/O") interfaces. The computer platform may also include an operating system and microinstruction code. The various processes and functions described herein may be either part of the microinstruction code or part of the application program, or any combination thereof, which may be executed by a CPU. In addition, various other peripheral units may be connected to the computer platform such as an additional data storage unit and a printing unit.

It is to be further understood that, because some of the constituent system components and methods depicted in the accompanying drawings are preferably implemented in software, the actual connections between the system components or the process function blocks may differ depending upon the manner in which embodiments of the present disclosure are programmed. Given the teachings herein, one of ordinary skill in the pertinent art will be able to contemplate these and similar implementations or configurations of the present disclosure.

Although the illustrative embodiments have been described herein with reference to the accompanying drawings, it is to be understood that the present disclosure is not limited to those precise embodiments, and that various changes and modifications may be effected therein by one of ordinary skill in the pertinent art without departing from the scope or spirit of the present disclosure. All such changes and modifications are intended to be included within the scope of the invention as set forth in the appended claims.

What is claimed is:

1. An apparatus for co-registration of multi-modal images in a three-dimensional environment, the apparatus comprising:
    a source of excitation light;
    a one-way mirror having a transmissive side disposed towards the excitation light for transmitting the excitation light and a reflective side for reflecting light received from a target;
    an electromagnetic-ray source disposed relative to the source of excitation light;
    an electromagnetic-ray transparent mirror having a light-reflective surface disposed towards a reflecting side of the one-way mirror and an electromagnetic-ray transmissive surface disposed towards the electromagnetic-ray source;
    a target location disposed towards the light-reflective surface of the electromagnetic-ray transparent mirror for locating a target and receiving the excitation light and the electromagnetic-rays;
    an electromagnetic-ray detector disposed on an opposite side of the target location relative to the electromagnetic-ray source for detecting electromagnetic-rays transmitted through the target; and
    a light detector disposed towards the reflective side of the one-way mirror for detecting light from the target,
    wherein the electromagnetic-ray wavelength is shorter than the wavelength of the light.

2. An apparatus as defined in claim 1 wherein the electromagnetic-ray source emits X-rays.

3. An apparatus as defined in claim 1 wherein the source of excitation light emits at least one of optical, fluorescent, coherent, diffusive and transmissive light.

4. An apparatus as defined in claim 1 wherein the light detector detects at least one of emitted and reflected light from the target.

5. An apparatus for co-registration of multi-modal images in a three-dimensional environment, the apparatus comprising:
    a source of excitation light;
    an electromagnetic-ray source disposed relative to the source of excitation light;
    an electromagnetic-ray transparent mirror having a first surface disposed towards the excitation light and a second surface disposed towards the electromagnetic-ray source;
    a target location disposed towards the first surface of the electromagnetic-ray transparent mirror for locating a target and receiving the excitation light and the electromagnetic rays;
    an electromagnetic-ray detector disposed on an opposite side of the target location relative to the electromagnetic-ray transparent mirror for detecting electromagnetic-rays transmitted through the target;
    a second electromagnetic-ray transparent mirror having a light-reflective surface disposed towards the target location;
    a light detector disposed towards the light-reflective surface of the second electromagnetic-ray transparent mirror for detecting light from the target; and
    a controller in signal communication with the source of excitation light for illuminating a target point with excitation light by capturing electromagnetic-ray image data of a scene from the electromagnetic-ray detector, identifying electromagnetic-ray image data associated with the target point, and projecting a beam of excitation light responsive to the electromagnetic-ray image data at the target point by converting image coordinates of the target point to light coordinates for directing the beam of excitation light, and processing the light coordinates to direct the beam of excitation light to the target point,
    wherein the electromagnetic-ray wavelength is shorter than the wavelength of the light.

6. An apparatus as defined in claim 5 wherein the electromagnetic-ray source emits X-rays.

7. An apparatus as defined in claim 5 wherein the source of excitation light emits at least one of optical, fluorescent, coherent, diffusive and transmissive light.

8. An apparatus as defined in claim 5 wherein the light detector detects transmitted light from the target.

9. An apparatus as defined in claim 5, further comprising a mirror disposed towards the excitation light for at least one of reflecting and redirecting the excitation light.

10. An apparatus as defined in claim 5, further comprising a mirror disposed towards the light-reflective surface of the second electromagnetic-ray transparent mirror for at least one of reflecting and redirecting the light from the target to the light detector.

11. An apparatus as defined in claim 5, further comprising at least one of gimbals and tracks for rotating the apparatus about a centrally disposed target.

12. A method for co-registration of multi-modal images in a three-dimensional environment, the method comprising:
    defining a frame of reference;
    providing electromagnetic-rays to a target relative to the frame of reference;
    detecting electromagnetic-rays transmitted by the target relative to the frame of reference;
    detecting light from the target relative to the frame of reference;
    providing co-registered electromagnetic-ray and light images of the target to a user; and
    providing excitation light to a point on the target relative to the frame of reference by capturing electromagnetic-ray image data, identifying electromagnetic-ray image data associated with the point on the target, and projecting a beam of excitation light responsive to the electromagnetic-ray image data at the point on the target by transmitting the excitation light through a non-reflecting side of a one-way mirror and reflecting light received from a target from a reflecting side of the one-way mirror,
    wherein the electromagnetic-ray wavelength is shorter than the wavelength of the light.

13. A method as defined in claim 12, further comprising redirecting the light to be detected from the target without redirecting the electromagnetic-rays to be detected from the target.

14. A method as defined in claim 12, further comprising redirecting the excitation light relative to the target without redirecting the provided electromagnetic-rays.

15. A method as defined in claim 12, further comprising:
    capturing X-ray image data; and
    identifying X-ray image data associated with the target.

16. A method for co-registration of multi-modal images in a three-dimensional environment, the method comprising:
    defining a frame of reference;
    providing electromagnetic-rays to a target relative to the frame of reference;
    detecting electromagnetic-rays transmitted by the target relative to the frame of reference;

detecting light from the target relative to the frame of reference;

providing co-registered electromagnetic-ray and light images of the target to a user; and providing excitation light to a point on the target responsive to the co-registered electromagnetic-ray image relative to the frame of reference, wherein providing excitation light comprises:

converting image coordinates of the target into light coordinates for directing the excitation light;

processing the light coordinates to direct the excitation light to the point on the target in a real scene;

transmitting the excitation light through a non-reflecting side of a one-way mirror; and reflecting light received from a target from a reflecting side of the one-way mirror.

17. A program storage device readable by machine, tangibly embodying a program of instructions executable by the machine to perform program steps for co-registration of multi-modal images in a three-dimensional environment, the program steps comprising:

defining a frame of reference;

providing electromagnetic-rays to a target relative to the frame of reference;

detecting electromagnetic-rays transmitted by the target relative to the frame of reference;

detecting light from the target relative to the frame of reference;

providing co-registered electromagnetic-ray and light images of the target to a user; and providing excitation light to a point on the target relative to the frame of reference by capturing electromagnetic-ray image data, identifying electromagnetic-ray image data associated with the point on the target, and projecting a beam of excitation light responsive to the electromagnetic-ray image data at the point on the target by transmitting the excitation light through a non-reflecting side of a one-way mirror and reflecting light received from a target from a reflecting side of the one-way mirror, wherein the electromagnetic-ray wavelength is shorter than the wavelength of the light.

18. A program storage device as defined in claim 17, the program steps further comprising redirecting the light to be detected from the target without redirecting the electromagnetic-rays to be detected from the target.

19. A program storage device as defined in claim 17, the program steps further comprising redirecting the excitation light relative to the target without redirecting the provided electromagnetic-rays.

20. A program storage device as defined in claim 17, the program steps further comprising:

capturing X-ray image data; and identifying X-ray image data associated with the target.

21. A program storage device readable by machine, tangibly embodying a program of instructions executable by the machine to perform program steps for co-registration of multi-modal images in a three-dimensional environment, the program steps comprising:

defining a frame of reference;

providing electromagnetic-rays to a target relative to the frame of reference;

detecting electromagnetic-rays transmitted by the target relative to the frame of reference;

detecting light from the target relative to the frame of reference;

providing co-registered electromagnetic-ray and light images of the target to a user; and providing excitation light to a point on the target responsive to the co-registered electromagnetic-ray image relative to the frame of reference, wherein the program step of providing excitation light comprises:

converting image coordinates of the target into light coordinates for directing the excitation light;

processing the light coordinates to direct the excitation light to the point on the target in a real scene;

transmitting the excitation light through a non-reflecting side of a one-way mirror; and reflecting light received from a target from a reflecting side of the one-way mirror.

* * * * *